(12) United States Patent
Sakaguchi et al.

(10) Patent No.: US 9,202,301 B2
(45) Date of Patent: Dec. 1, 2015

(54) MEDICAL IMAGE DISPLAY APPARATUS AND X-RAY DIAGNOSIS APPARATUS

(75) Inventors: Takuya Sakaguchi, Utsunomiya (JP); Manabu Tanaka, Nasushiobara (JP); Nobuyuki Matsumoto, Inagi (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 297 days.

(21) Appl. No.: 13/593,679

(22) Filed: Aug. 24, 2012

(65) Prior Publication Data

US 2013/0230136 A1 Sep. 5, 2013

(30) Foreign Application Priority Data

Aug. 25, 2011 (JP) .................................. 2011-183451

(51) Int. Cl.
*G06T 15/00* (2011.01)
*A61B 6/02* (2006.01)
*H04N 13/00* (2006.01)
*H04N 13/04* (2006.01)
(Continued)

(52) U.S. Cl.
CPC ................. *G06T 15/00* (2013.01); *A61B 6/022* (2013.01); *A61B 6/12* (2013.01); *A61B 6/466* (2013.01); *A61B 6/487* (2013.01); *A61B 6/504* (2013.01); *H04N 13/00* (2013.01); *H04N 13/0014* (2013.01); *H04N 13/0022* (2013.01); *H04N 13/0456* (2013.01); *H04N 2013/0081* (2013.01)

(58) Field of Classification Search
CPC .......... H04N 13/00; H04N 2013/0081; H04N 13/0022; H04N 13/0456; H04N 13/0014; G06T 15/00; A61B 6/022

USPC ...................... 345/419; 378/41; 382/128, 130
See application file for complete search history.

(56) References Cited

U.S. PATENT DOCUMENTS 6,590,573 B1 * 7/2003 Geshwind ...................... 345/419
6,927,769 B2 * 8/2005 Roche, Jr. ...................... 345/419
(Continued)

FOREIGN PATENT DOCUMENTS

CN         101164348 A      4/2008
JP         2005-86414       3/2005
(Continued)

OTHER PUBLICATIONS

Office Action issued on Dec. 29, 2014 in the corresponding Chinese Patent Application No. 201210303856.7.

*Primary Examiner* — Phu K Nguyen
(74) *Attorney, Agent, or Firm* — Oblon, McClelland, Maier & Neustadt, L.L.P.

(57) ABSTRACT

A medical image display apparatus according to an embodiment includes a display unit, a generating unit, and a display controlling unit. The display unit three-dimensionally displays a group of disparity images generated from three-dimensional medical image data. The generating unit determines a display position of the group of disparity images to be three-dimensionally displayed on the display unit in terms of a depth direction with respect to a display surface of the display unit and generates the group of disparity images from the three-dimensional medical image data so as to realize the determined display position. The display controlling unit three-dimensionally displays the group of disparity images and two-dimensionally displays a medical image different from the group of disparity images, on the display unit.

21 Claims, 10 Drawing Sheets

(51) Int. Cl.
*A61B 6/12* (2006.01)
*A61B 6/00* (2006.01)

(56) References Cited

U.S. PATENT DOCUMENTS

| | | | |
|---|---|---|---|
| 7,412,023 B2 | 8/2008 | Ohishi et al. | |
| 7,812,815 B2 * | 10/2010 | Banerjee et al. | 345/156 |
| 8,090,171 B2 * | 1/2012 | Kramp et al. | 382/128 |
| 8,111,906 B2 * | 2/2012 | Song et al. | 382/154 |
| 8,411,931 B2 * | 4/2013 | Zhou et al. | 382/154 |
| 8,488,853 B2 * | 7/2013 | Sato et al. | 382/128 |
| 8,493,437 B2 * | 7/2013 | Getty | 348/51 |
| 8,526,694 B2 * | 9/2013 | Pajeau | 382/130 |
| 8,659,645 B2 * | 2/2014 | Tsukagoshi et al. | 348/51 |
| 8,743,109 B2 * | 6/2014 | Blank et al. | 345/419 |
| 8,761,471 B2 * | 6/2014 | Ozawa et al. | 382/128 |
| 8,854,356 B2 * | 10/2014 | Oyagi et al. | 345/419 |
| 8,928,728 B2 * | 1/2015 | Wiener et al. | 348/14.12 |
| 2008/0055305 A1 | 3/2008 | Blank et al. | |

FOREIGN PATENT DOCUMENTS

| | | | |
|---|---|---|---|
| JP | 2011-158029 | * | 7/2011 |
| JP | 4901531 | | 1/2012 |

* cited by examiner

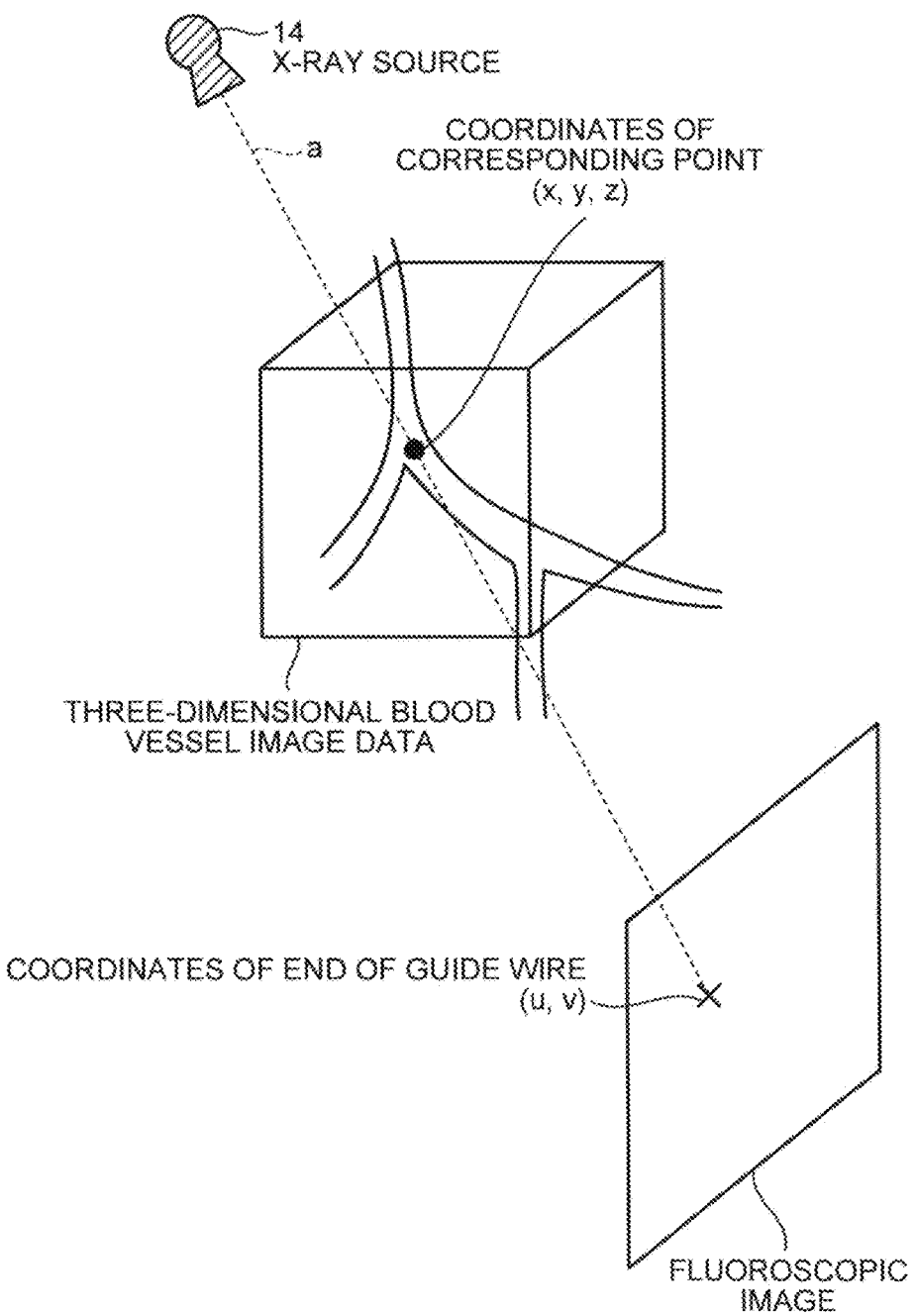

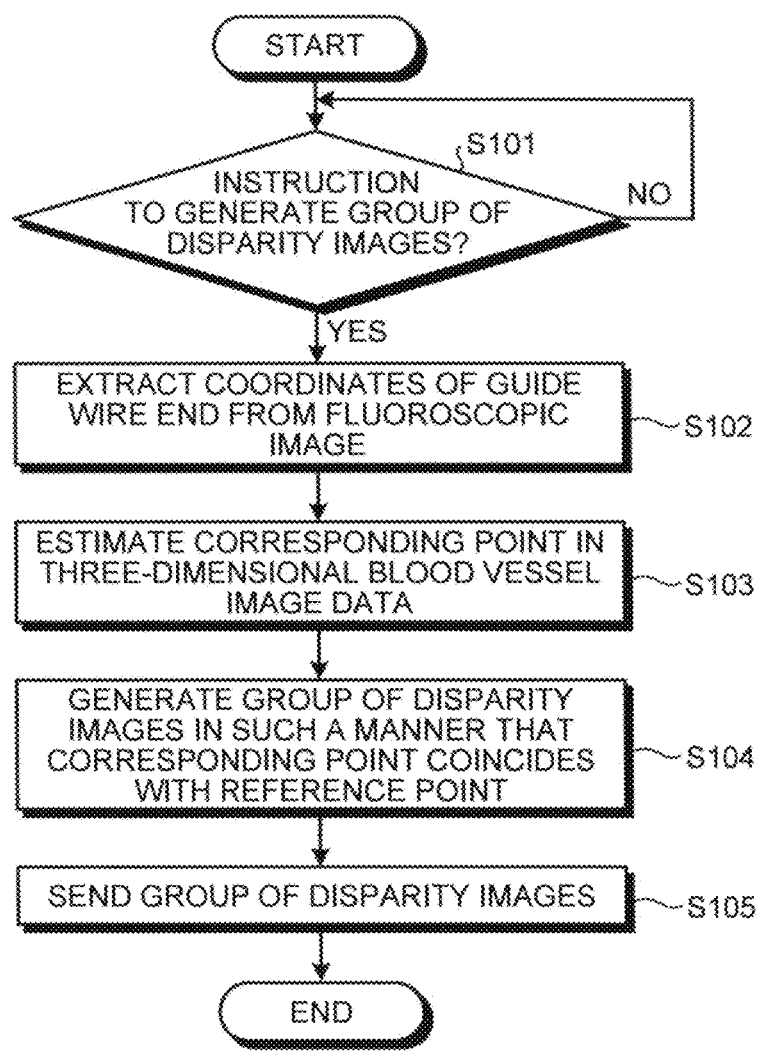

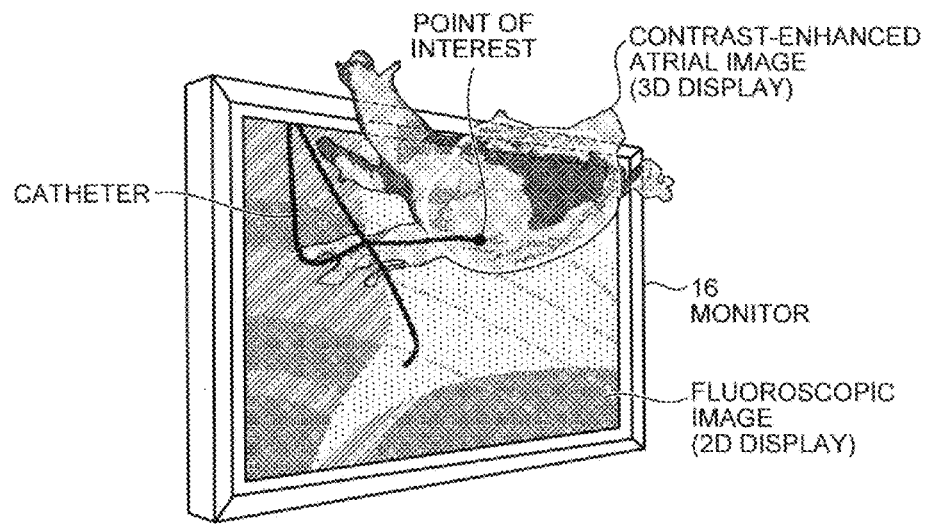
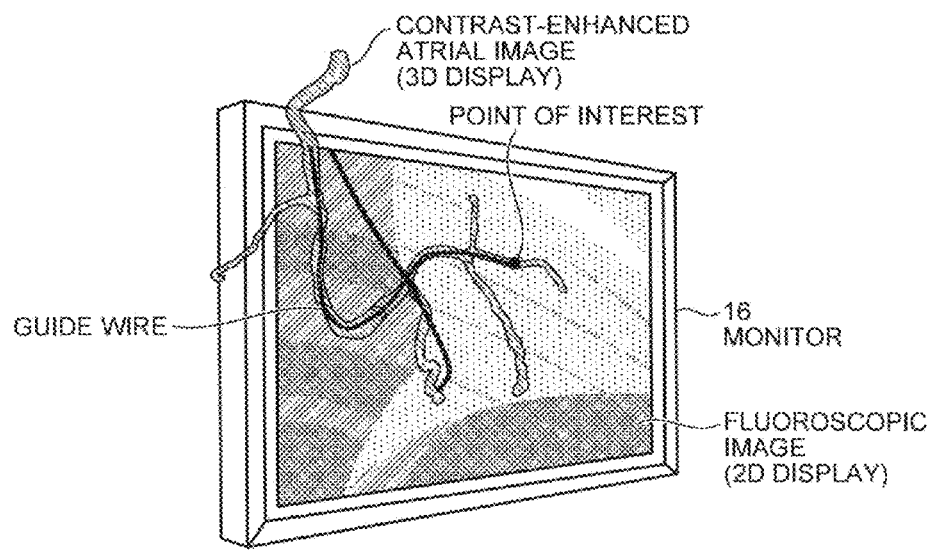

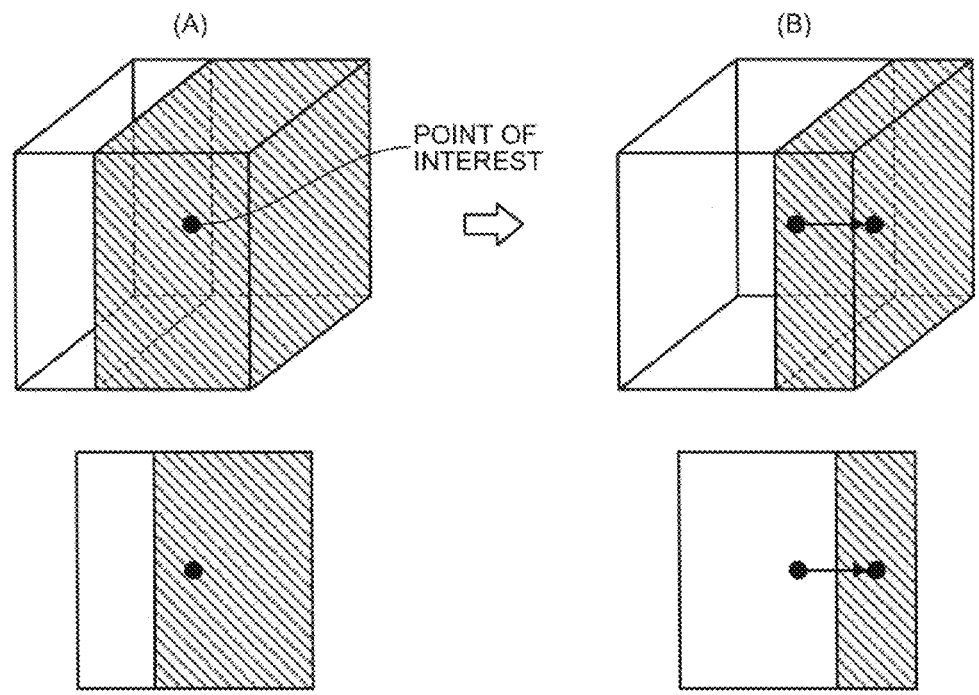
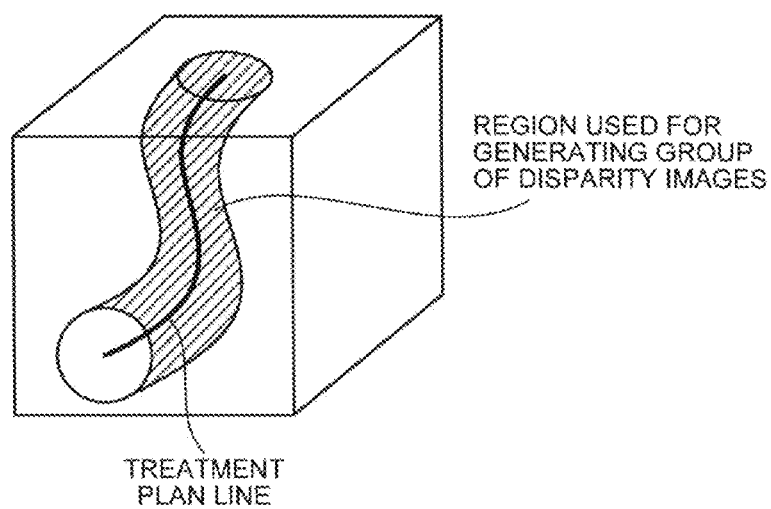

US 9,202,301 B2

MEDICAL IMAGE DISPLAY APPARATUS AND X-RAY DIAGNOSIS APPARATUS

CROSS-REFERENCE TO RELATED APPLICATIONS

This application is based upon and claims the benefit of priority from Japanese Patent Application No. 2011-183451, filed on Aug. 25, 2011; the entire contents of which are incorporated herein by reference.

FIELD

Embodiments described herein relate generally to a medical image display apparatus and an X-ray diagnosis apparatus.

BACKGROUND

Ischemic heart disease is one of the world's major diseases. In recent years, endovascular therapy, which is minimally invasive, is getting more popular as a therapeutic method for ischemic heart disease. Endovascular therapy is usually practiced with X-ray fluoroscopy, and an X-ray diagnosis apparatus is used as an image-guide tool. These days a method called "roadmap" is often used. The "roadmap" is a method by which a fluoroscopic image is displayed as being superimposed in a real-time manner on an angiographic image represented by a still image. In the fluoroscopic image, a guide wire or the like that is advanced in a blood vessel by a medical doctor is rendered.

Further, one of different types of roadmap is called a 3D roadmap method. According to the 3D roadmap method, a two-dimensional projection image generated from three-dimensional blood vessel image data is used as an angiographic image. In other words, the 3D roadmap is a method by which a fluoroscopic image is displayed as being superimposed in a real-time manner on the two-dimensional projection image generated according to a movement of an X-ray diagnosis apparatus (e.g., a movement of a bed or a rotation of a C-arm). The three-dimensional blood vessel image data may be images acquired by rotating the C-arm of the X-ray diagnosis apparatus or may be Computed Tomography (CT) images acquired by an X-ray CT apparatus.

However, the images displayed on a monitor are merely two-dimensional images, according to any of these roadmap methods. Thus, when a medical doctor looks at a monitor while advancing a guide wire, for example, although he/she is able to perceive two-dimensional information, the information in the depth direction is lost. As a result, the medical doctor is still not able to sufficiently understand, for example, in which direction the guide wire should be advanced at a branching portion of the blood vessel.

Incidentally, 3D monitor technology has become more common in recent years. 3D monitors are capable of providing viewers with a stereoscopic view of images. For example, the viewers are able to visually perceive a pop-up feel and a depth-feel of the images. Methods that use special glasses as well as glass-free methods are known.

BRIEF DESCRIPTION OF THE DRAWINGS

FIG. 6 is a drawing for explaining an estimation of a corresponding point according to the first embodiment;

FIG. 7 is a flowchart of a disparity image group generating process according to the first embodiment;

FIG. 8 is a drawing for explaining an example of a display of a stereoscopic roadmap image according to the first embodiment;

FIG. 9 is a drawing for explaining another example of the display of a stereoscopic roadmap image according to the first embodiment;

FIG. 12 is another drawing for explaining the generation of a group of disparity images according to the third embodiment;

FIG. 13 is yet another drawing for explaining the generation of a group of disparity images according to the third embodiment.

DETAILED DESCRIPTION

A medical image display apparatus according to an embodiment includes a display unit, a generating unit, and a display controlling unit. The display unit three-dimensionally displays a group of disparity images generated from three-dimensional medical image data. The generating unit determines a display position of the group of disparity images to be three-dimensionally displayed on the display unit in terms of a depth direction with respect to a display surface of the display unit and generates the group of disparity images from the three-dimensional medical image data so as to realize the determined display position. The display controlling unit three-dimensionally displays the group of disparity images and two-dimensionally displays a medical image different from the group of disparity images, on the display unit.

In the following sections, exemplary embodiments of a medical image display apparatus and an X-ray diagnosis apparatus will be explained in detail, with reference to the accompanying drawings. First, some of the terms used below will be defined. A "fluoroscopic image" is a moving image generated by detecting X-rays that have transmitted through an examined subject (hereinafter, "subject") while using an X-ray detector and is displayed two-dimensionally in a real-time manner. Similarly, like a fluoroscopic image, a "radiographed image" is also a moving image generated by detecting X-rays that have transmitted through a subject while using an X-ray detector; however, a higher dose of X-rays is used for a radiographed image than for a fluoroscopic image. The dose of X-rays to be used is determined, for example, depending on whether it is necessary to have a record. For example, when it is necessary to have a record, a "radiographed image", which uses a higher dose, is acquired. Although a "fluoroscopic image" and a "radiographed image" are each a moving image, the broader term "X-ray image" includes "still image", in addition to "fluoroscopic image" and "radiographed image". The exemplary embodiments will be explained below while mainly using "fluoroscopic image"; however, the disclosed embodiments are not limited to those examples and are similarly applicable to "X-ray images" in a broader sense. Further, such images that are generally referred to as a "transmission image" and a "two-dimensional image" are also included in "X-ray images".

Figure 1:
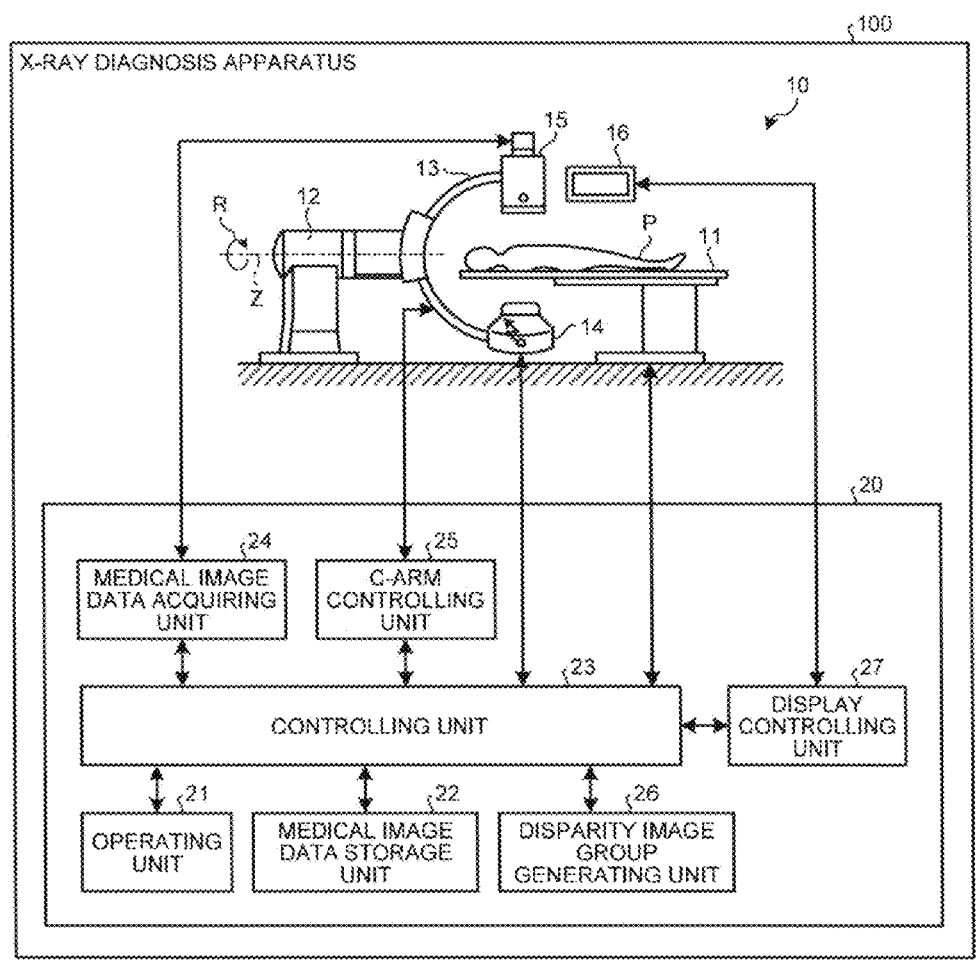
FIG. 1 is a drawing for explaining an exemplary configuration of an X-ray diagnosis apparatus according to a first embodiment.

FIG. 1 is a drawing for explaining an exemplary configuration of an X-ray diagnosis apparatus 100 according to a first embodiment. As shown in FIG. 1, the X-ray diagnosis apparatus 100 includes a gantry unit 10 and a computer system 20. As shown in FIG. 1, the gantry unit 10 includes a bed (patient table) 11, a gantry 12, a C-arm 13, an X-ray source 14, an X-ray detector 15, and a monitor 16.

The bed 11 is movable in a vertical direction and a horizontal direction, and a subject P is placed thereon. The gantry 12 supports the C-arm 13. The C-arm 13 is rotatable in the R direction shown with the arrow while using a Z-axis as the center and is configured to hold the X-ray source 14 and the X-ray detector 15 opposing each other. The X-ray source 14 includes an X-ray tube that radiates X-rays and a collimator. The X-ray detector 15 detects X-rays that are radiated from the X-ray source 14 and have transmitted through the subject P. The monitor 16 displays, for example, a stereoscopic roadmap image in which a fluoroscopic image is displayed as being superimposed on angiographic images capable of providing a stereoscopic view. As explained later, in the first embodiment, the stereoscopic roadmap image refers to an image obtained by displaying stereoscopic images and a fluoroscopic image that are superimposed together, the stereoscopic image being three-dimensionally displayed so as to provide a stereoscopic view by using two or more two-dimensional projection images generated from three-dimensional blood vessel image data.

In this situation, the monitor 16 according to the first embodiment is a three-dimensional (3D) monitor with which the viewer is able to have a stereoscopic view of the images. For example, the monitor 16 displays the images three-dimensionally by using a shutter method.

Figure 2:
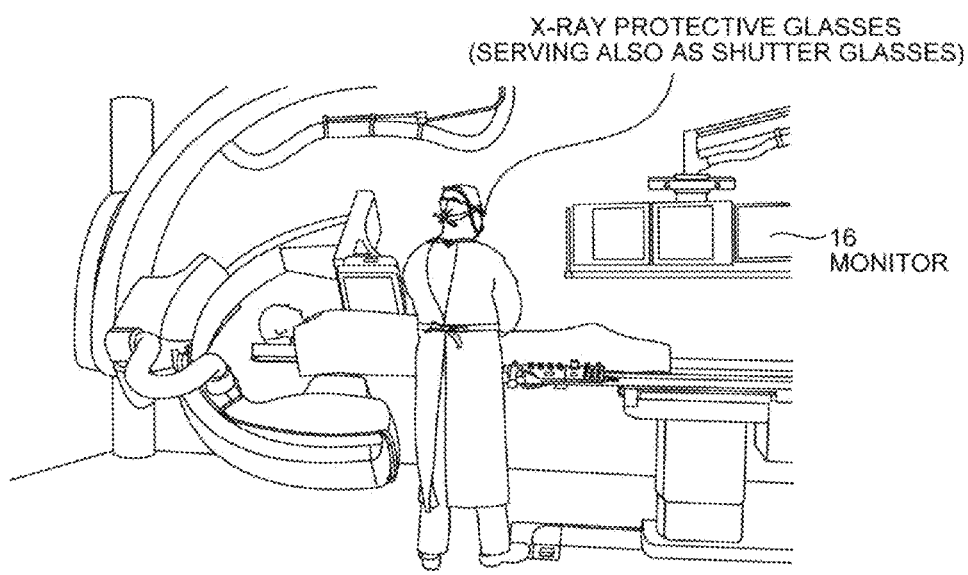
FIG. 2 is a drawing for explaining a monitor according to the first embodiment.

FIG. 2 is a drawing for explaining the monitor 16 according to the first embodiment. As shown in FIG. 2, a medical doctor who looks at the monitor 16 wears shutter glasses as stereoscopic-view glasses that can also serve as X-ray protective glasses. In this situation, the monitor 16 displays images to be viewed by the right eye (hereinafter, "right-eye images") and images to be viewed by the left eye (hereinafter, "left-eye images") alternately, for example, at 120 Hz. Further, the monitor 16 is provided with an infrared ray emitting unit, which controls emissions of infrared rays in synchronization with the timing with which the right-eye images and the left-eye images are switched. The shutter glasses are provided with an infrared ray receiving unit. The infrared ray receiving unit receives the infrared rays emitted from the infrared ray emitting unit and switches shutters into a light transmitting state and a light blocking state alternately, the shutters each being attached to a left part and a right part of the shutter glasses.

The 3D monitor does not necessarily have to use the shutter method. For example, the 3D monitor may use a polarization glasses method or any other method capable of providing a glass-free stereoscopic view by using a light beam controller such as a lenticular lens (cf. for example, JP-A 2005-86414 (KOKAI)).

Returning to the description of FIG. 1, the computer system 20 includes an operating unit 21, a medical image data storage unit 22, a controlling unit 23, a medical image data acquiring unit 24, a C-arm controlling unit 25, a disparity image group generating unit 26, and a display controlling unit 27.

The operating unit 21 is configured with a control panel, a foot switch, and the like and is configured to receive inputs of various types of operations performed on the X-ray diagnosis apparatus 100 from an operator. More specifically, the operating unit 21 according to the first embodiment receives, for example, an instruction to acquire fluoroscopic image data or an instruction to display a stereoscopic roadmap image. The medical image data storage unit 22 stores therein, for example, the three-dimensional blood vessel image data used for displaying the stereoscopic roadmap image. The controlling unit 23 exercises overall control of the X-ray diagnosis apparatus 100.

The medical image data acquiring unit 24 acquires the three-dimensional blood vessel image data and the fluoroscopic image data used for displaying the stereoscopic roadmap image. In the first embodiment, the three-dimensional blood vessel image data is acquired in advance before the control is exercised to display the stereoscopic roadmap image, whereas the fluoroscopic image data is acquired in a real-time manner during the display control of the stereoscopic roadmap image.

For example, when having received an instruction to acquire three-dimensional blood vessel image data, the medical image data acquiring unit 24 controls the X-ray source 14, the X-ray detector 15, and the C-arm controlling unit 25 so as to acquire three-dimensional blood vessel image data. The medical image data acquiring unit 24 stores the acquired three-dimensional blood vessel image data into the medical image data storage unit 22. In the first embodiment, the example is explained in which the three-dimensional blood vessel image data is acquired by rotating the C-arm 13 included in the X-ray diagnosis apparatus 100; however, the disclosed embodiments are not limited to this example. For instance, it is acceptable to use three-dimensional blood vessel image data acquired in advance by an X-ray CT apparatus that is different from the X-ray diagnosis apparatus 100.

Further, when having received an instruction to acquire fluoroscopic image data from the display controlling unit 27, the medical image data acquiring unit 24 controls the X-ray source 14, the X-ray detector 15, and the C-arm controlling unit 25 so as to acquire fluoroscopic image data. Further, the medical image data acquiring unit 24 sends the acquired fluoroscopic image data to the disparity image group generating unit 26 and the display controlling unit 27. Under the control of the medical image data acquiring unit 24, the C-arm controlling unit 25 controls the rotation of the C-arm 13 and the like.

The disparity image group generating unit 26 generates right-eye images and left-eye images serving as a group of disparity images, from the three-dimensional blood vessel image data. More specifically, when having received an instruction to generate the group of disparity images used for displaying the stereoscopic roadmap image from the display controlling unit 27, the disparity image group generating unit 26 refers to the medical image data storage unit 22 and obtains the three-dimensional blood vessel image data acquired in advance. Further, the disparity image group generating unit 26 generates the right-eye images and the left-eye images from the obtained three-dimensional blood vessel image data and sends the generated right-eye images and left-eye images to the display controlling unit 27. The disparity image group generating process performed by the disparity image group generating unit 26 will be explained later.

The display controlling unit 27 displays, on the monitor 16, the stereoscopic roadmap image in which the fluoroscopic image is displayed as being superimposed on the group of disparity images represented by the three-dimensional blood vessel images. For example, when having received an instruction to display the stereoscopic roadmap image via the operating unit 21, the display controlling unit 27 sends an instruction to acquire the fluoroscopic image data to the medical image data acquiring unit 24 and receives the fluoroscopic image data acquired in the real-time manner from the medical image data acquiring unit 24. Further, the display controlling unit 27 sends an instruction to generate the group of disparity images to the disparity image group generating unit 26 and receives the right-eye images and the left-eye images generated from the three-dimensional blood vessel image data from the disparity image group generating unit 26. After that, the display controlling unit 27 displays, on the monitor 16, the fluoroscopic image and the right-eye images and the left-eye images generated from the three-dimensional blood vessel image data that are superimposed together.

In this situation, the monitor 16 three-dimensionally displays the three-dimensional blood vessel images so as to provide a stereoscopic view by displaying the group of disparity images, whereas the monitor 16 two-dimensionally displays the fluoroscopic image. In other words, at a time to display a right-eye image, the display controlling unit 27 displays, on the monitor 16, the fluoroscopic image sent from the medical image data acquiring unit 24 and the right-eye image sent from the disparity image group generating unit 26 that are superimposed together, while the pixel values thereof are weighted or the like. Similarly, at a time to display a left-eye image, the display controlling unit 27 displays, on the monitor 16, the fluoroscopic image sent from the medical image data acquiring unit 24 and the left-eye image sent from the disparity image group generating unit 26 that are superimposed together, while the pixel values thereof are weighted or the like.

Next, the disparity image group generating process performed by the disparity image group generating unit 26 according to the first embodiment will be explained in detail. A conventional X-ray diagnosis apparatus is configured to display, on a regular 2D monitor (not a 3D monitor), a 3D roadmap image in which a two-dimensional fluoroscopic image is superimposed merely on a two-dimensional projection image.

Figure 3:
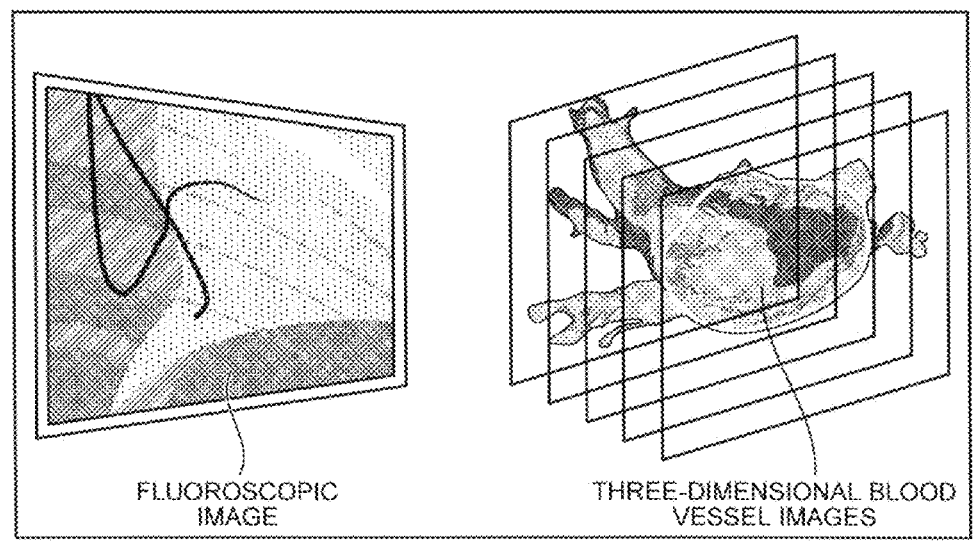
FIG. 3 is a drawing for explaining a fluoroscopic image and three-dimensional blood vessel images according to the first embodiment.

In contrast, the X-ray diagnosis apparatus 100 according to the first embodiment displays the stereoscopic roadmap image. In other words, the X-ray diagnosis apparatus 100 according to the first embodiment displays, on the 3D monitor, the stereoscopic roadmap image obtained by displaying the stereoscopic images and the two-dimensional fluoroscopic image that are superimposed together, the stereoscopic images being three-dimensionally displayed so as to provide the stereoscopic view by using the two or more two-dimensional projection images generated from the three-dimensional blood vessel image data. FIG. 3 is a drawing for explaining the fluoroscopic image and the three-dimensional blood vessel images according to the first embodiment. In this situation, as shown in FIG. 3, the fluoroscopic image is displayed two-dimensionally while information in the depth direction is lost, whereas the three-dimensional blood vessel images are displayed three-dimensionally while information in the depth direction is kept. Thus, the X-ray diagnosis apparatus 100 according to the first embodiment determines the display positions of the three-dimensional blood vessel images displayed three-dimensionally in terms of the depth direction (the depth direction with respect to the display surface of the monitor 16), based on the fluoroscopic image displayed two-dimensionally.

Figure 4:
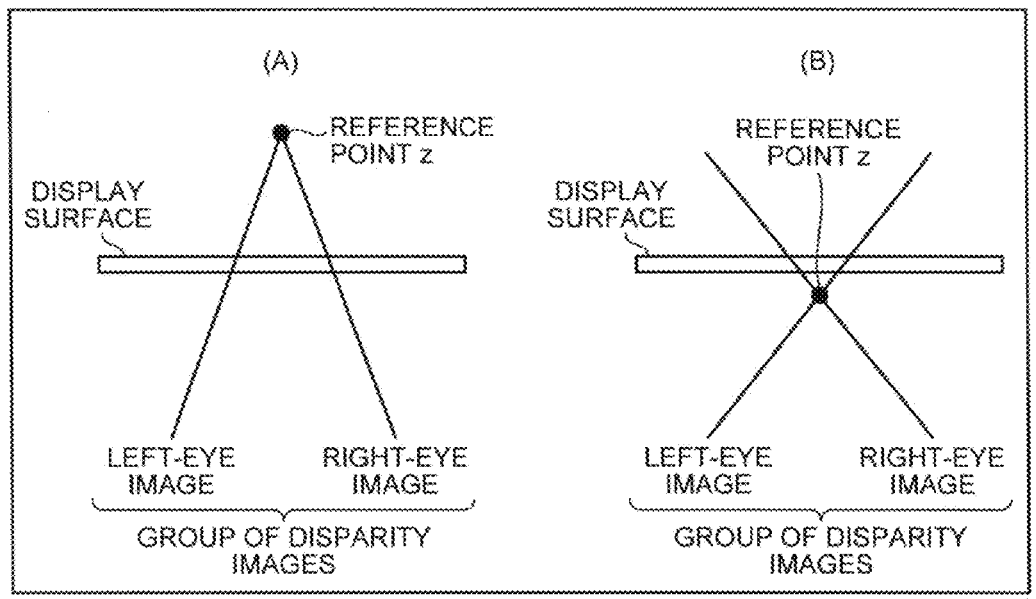
FIG. 4 is a drawing for explaining a reference point according to the first embodiment.

In this situation, images capable of providing a stereoscopic view have a "reference point" at which the disparity between the left eye and the right eye is zero. FIG. 4 is a drawing for explaining the reference point according to the first embodiment. For instance, in one example, as shown in FIG. 4(A), right-eye images and left-eye images may be generated while a reference point z is set in a position in the back of the display surface of the monitor 16. In another example, as shown in FIG. 4(B), right-eye images and left-eye images may be generated while a reference point z is set in a position to the front of the display surface of the monitor 16. In yet another example, right-eye images and left-eye images may be generated while a reference point z is set on the display surface of the monitor 16. It is possible to arbitrarily determine the position in which the reference point is set. As explained above, the reference point is the point at which the disparity is zero and is a point where the images are easy to see for the viewer.

For this reason, when displaying on the 3D monitor the fluoroscopic image and the three-dimensional blood vessel images that are superimposed together, the X-ray diagnosis apparatus 100 according to the first embodiment generates the group of disparity images in such a manner that a corresponding point in the three-dimensional blood vessel image data corresponding to a point of interest in the fluoroscopic image coincides with the reference point (or in such a manner that the corresponding point is positioned near the reference point). For example, if the reference point is set on the display surface, the point of interest in the fluoroscopic image and the corresponding point in the three-dimensional blood vessel images overlap each other on the same display surface.

Figure 5:
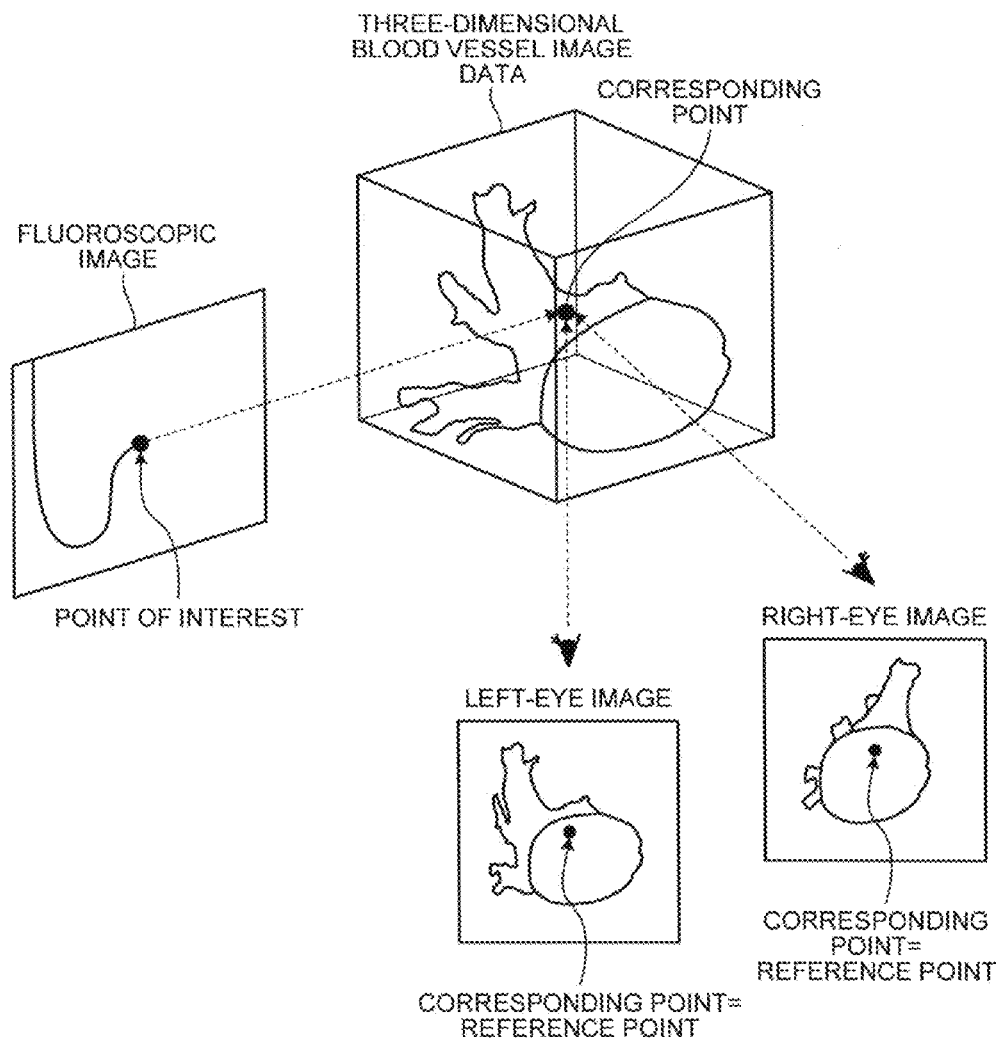
FIG. 5 is a drawing for explaining generation of a group of disparity images according to the first embodiment.

FIG. 5 is a drawing for explaining the generation of the group of disparity images according to the first embodiment. As shown in FIG. 5, because the information in the depth direction is lost from the fluoroscopic image, it is not clear in what position in terms of the depth direction, the point of interest in the fluoroscopic image is present. In contrast, because the information in the depth direction is kept in the three-dimensional blood vessel image data, it is possible to identify in what position in terms of the depth direction, the corresponding point corresponding to the point of interest in the fluoroscopic image is present. Thus, when the group of disparity images is generated while the position in the depth direction is aligned in such a manner that the corresponding point coincides with the reference point at which the images are easy to see for the viewer, a stereoscopic roadmap image in which the point of interest is easy to see for the viewer is obtained. To make the corresponding point precisely coincide with the reference point, it may be necessary to align not only the position in the depth direction, but also the position on the display surface perpendicular to the depth direction. In that situation, it may be further necessary to align the positions between the fluoroscopic image and the three-dimensional blood vessel images. However, it is acceptable to align the position in the depth direction in such a manner that the corresponding point is positioned near the reference point, instead of making the corresponding point precisely coincide with the reference point. For example, it is acceptable to align the position in the depth direction in such a manner that the corresponding point is positioned at least on a reference plane that contains the reference point. The position alignment will be explained below more specifically.

In the first embodiment, the disparity image group generating unit 26 performs a "first stage" at which a point of interest is extracted from the fluoroscopic image, a "second stage" at which the corresponding point in the three-dimensional blood vessel image data that corresponds to the point of interest is estimated, and a "third stage" at which a group of disparity images is generated in such a manner that the estimated corresponding point coincides with the reference point. The methods that can be used at the "first stage" include "Method A1 by which the point of interest is automatically extracted from the fluoroscopic image" and "Method A2 by which the point of interest is extracted from the fluoroscopic image by allowing the operator who views the fluoroscopic image displayed on the monitor 16 to designate the point of interest on the display screen of the monitor 16". The methods that can be used at the "second stage" include "Method B1 by which the corresponding point in the three-dimensional blood vessel image data is estimated based on the assumption that the point of interest is present in a blood vessel" and "Method B2 by which the corresponding point in the three-dimensional blood vessel image data is estimated based on the assumption that the point of interest is positioned near a treatment plan line (that is, for example, drawn by a medical doctor in advance to indicate that "the blood vessel in this area is to be treated")". It is possible to use any of these methods in combination. In the following sections, an example using a combination of Method A1 and Method B1 will be principally explained.

First, as an example of the "first stage" at which the point of interest is extracted from the fluoroscopic image, Method A1 will be explained. In this situation, the "point of interest" is a point in which the viewer is interested in the fluoroscopic image. Examples of the point of interest include the position of a tip (end) of a guide wire or a catheter, and the position of a stent, a balloon, or a valve. In the first embodiment, the disparity image group generating unit 26 extracts coordinates of a tip (end) of a guide wire (hereinafter, "guide wire tip"), as the point of interest. It is possible to extract any other point of interest in the same manner.

First, the disparity image group generating unit 26 receives the fluoroscopic image data from the medical image data acquiring unit 24. The fluoroscopic image data is, for example, moving image data having approximately 5 frames to 30 frames per second. Subsequently, the disparity image group generating unit 26 identifies an image of the guide wire in each of the frames by using an image processing technique.

For example, the disparity image group generating unit 26 sharpens the images of the guide wire by performing an enhancement process on each of the frames. For example, the disparity image group generating unit 26 first reduces density unevenness in each of the images of the guide wire by performing a non-linear luminosity transformation and subsequently performs an image filtering process thereon so as to extract components having a high spatial frequency. The image filtering process is performed to eliminate gradations that are smooth and in a broad area and to keep only fluctuating components that are regional and fine.

After that, the disparity image group generating unit 26 identifies the images of the guide wire by performing a pattern extracting process on each of the frames. For example, the disparity image group generating unit 26 performs a threshold processing process on the pixel values or performs a spatial filtering process. Thus, the disparity image group generating unit 26 extracts the image of the guide wire from each of the frames and calculates a two-dimensional curve expressing the shape of the image of the guide wire in each of the frames. Further, based on the coordinate values of each of the points on the two-dimensional curve, the disparity image group generating unit 26 extracts the coordinates of the guide wire tip, which is positioned at an end of the two-dimensional curve.

Next, as an example of the "second stage" at which the corresponding point in the three-dimensional blood vessel image data is estimated, Method B1 will be explained. It is assumed that the positional alignment on the display surface between the fluoroscopic image and the three-dimensional blood vessel images has already been completed. FIG. 6 is a drawing for explaining the estimation of the corresponding point according to the first embodiment. As shown in FIG. 6, the positional relationship between the three-dimensional blood vessel image data and the fluoroscopic image is the same as the positional relationship between the three-dimensional blood vessel image data and a three-dimensional projection image generated from the three-dimensional blood vessel image data. In other words, all the information that is on a straight line "a" connecting coordinates (u,v) of the guide wire tip to the X-ray source 14 and that passes through the three-dimensional blood vessel image data is projected on the coordinates (u,v) of the guide wire tip in the fluoroscopic image.

Thus, the disparity image group generating unit 26 first calculates the straight line "a" connecting the coordinates (u,v) of the guide wire tip to the X-ray source 14. It is possible to obtain the coordinates of the X-ray source 14 from, for example, the C-arm controlling unit 25. Subsequently, based on the assumption that the point of interest is present in a blood vessel, the disparity image group generating unit 26 conducts a search along the straight line "a" passing through the three-dimensional blood vessel image data so as to identify a point at which the straight line "a" intersects the blood vessel. After that, the disparity image group generating unit 26 estimates the coordinates of the specified point to be coordinates (x,y,z) of the corresponding point that corresponds to the point of interest. Because the X-ray source 14 is supposed to have been moved by the medical doctor to a position where the point of interest is easy to see, it is generally considered that there is only one set of coordinates at which the straight line "a" intersects the blood vessel. Also, by performing, for example, a threshold processing process on the three-dimensional blood vessel image data, the disparity image group generating unit 26 is able to identify the blood vessel out of the three-dimensional blood vessel image data.

The disparity image group generating unit 26 according to the exemplary embodiment is able to estimate the coordinates of the corresponding point even in the situation where two or more points are identified as the points at which the straight line "a" intersects the blood vessel. For example, if the blood vessel curves radically or curves in the depth direction, two or more points may be identified as the points (candidate points) at which the straight line "a" intersects the blood vessel. In that situation, the disparity image group generating unit 26 estimates the coordinates of the corresponding point by utilizing the characteristic where the movement of the guide wire does not make a sudden leap and should be continuous along the blood vessel. For example, the disparity image group generating unit 26 is configured to estimate the coordinates of the guide wire tip (i.e., the coordinates of the corresponding point) along a time sequence. For this reason, the disparity image group generating unit 26 extracts a blood vessel center line from the three-dimensional blood vessel image data and calculates a distance between the corresponding point estimated at an immediately-preceding point-in-time and each of the candidate points, along the blood vessel center line. Further, the disparity image group generating unit 26 selects one of the candidate points of which the calculated distance was shortest as the corresponding point.

When Method B2 is used at the "second stage", the disparity image group generating unit 26 conducts a search along the straight line "a" passing through the three-dimensional blood vessel image data, so as to identify a point at which the straight line "a" intersects the blood vessel, based on the assumption that the point of interest is positioned near the treatment plan line.

Next, the "third stage" at which the group of disparity images is generated in such a manner that the estimated corresponding point coincides with the reference point will be explained. The disparity image group generating unit 26 generates the right-eye images and the left-eye images by performing a rendering process on the three-dimensional blood vessel image data. The rendering process is performed according to rendering conditions that have been set. Thus, for example, the disparity image group generating unit 26 sets, in advance, a viewpoint position for the right eye and a viewpoint position for the left eye (or a disparity angle between a line of sight of the right eye and a line of sight of the left eye), as well as a projection method, as the rendering conditions. Examples of the projection method include a perspective projection method and a parallel projection method. Further, examples of the rendering process include a volume rendering process and a surface rendering process. For example, the volume rendering process is a method by which a two-dimensional image that reflects three-dimensional information is generated directly from three-dimensional medical image data. In contrast, the surface rendering process is a method by which a model is structured by extracting target data from three-dimensional medical image data so that a two-dimensional image that reflects three-dimensional information is generated based on the structured model.

Further, the disparity image group generating unit 26 performs the rendering process in such a manner that the corresponding point estimated at the "second stage" coincides with the reference points appearing in the right-eye images and the left-eye images (or in such a manner that the corresponding point is positioned on the reference plane). For example, the disparity image group generating unit 26 performs the rendering process in such a manner that the pixel of the corresponding point is positioned in the position of the reference point that is set in advance in each of both the right-eye and the left-eye images. Alternatively, the disparity image group generating unit 26 performs the rendering process in such a manner that the reference point in each of the right-eye and the left-eye images is set in the pixel of the corresponding point.

FIG. 7 is a flowchart of a disparity image group generating process according to the first embodiment. As shown in FIG. 7, when having received an instruction to generate a group of disparity images from the display controlling unit 27 (step S101: Yes), the disparity image group generating unit 26 first extracts the coordinates of the guide wire tip from the fluoroscopic image (step S102), and subsequently estimates a corresponding point in the three-dimensional blood vessel image data (step S103).

After that, the disparity image group generating unit 26 generates a group of disparity images in such a manner that the estimated corresponding point coincides with the reference point (step S104) and sends the generated group of disparity images to the display controlling unit 27 (step S105).

Figure 10:
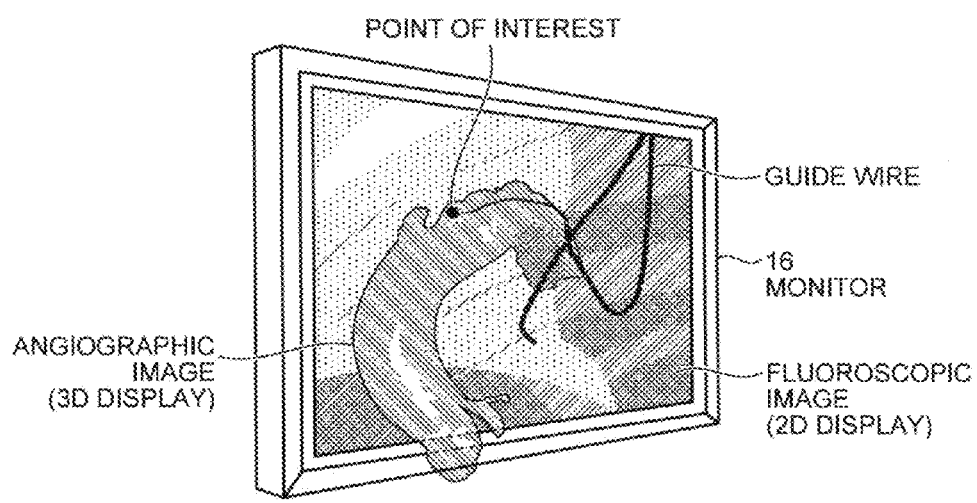
FIG. 10 is a drawing for explaining yet another example of the display of a stereoscopic roadmap image according to the first embodiment.

When the generated group of disparity images has been sent to the display controlling unit 27 in this manner, the display controlling unit 27 displays a stereoscopic roadmap image as shown in, for example, FIGS. 8 to 10. FIGS. 8 to 10 are drawings for explaining examples of displays of a stereoscopic roadmap image according to the first embodiment. FIG. 8 is an example of a display of a stereoscopic roadmap image used for an arrhythmia ablation treatment. FIG. 9 is an example of a display of a stereoscopic roadmap image used for the coronary artery in the heart. FIG. 10 is an example of a display of a stereoscopic roadmap image used for an aorta.

Additional Function 1 of First Embodiment

In the first embodiment, the disparity image group generating unit 26 follows the point of interest in the fluoroscopic image and generates the group of disparity images at certain times, according to the movement of the point of interest. For example, when the medical doctor advances the guide wire within the blood vessel, the point of interest in the fluoroscopic image also moves. Thus, the disparity image group generating unit 26 follows the coordinates of the guide wire tip by using Method A2 described above, so as to estimate a corresponding point that corresponds to a new set of coordinates of the guide wire tip and to generate a group of disparity images at certain times in such a manner that the estimated corresponding point coincides with the reference point. Further, the disparity image group generating unit 26 sends the newly-generated group of disparity images to the display controlling unit 27 at certain times. As a result, when the guide wire is advanced, for example, the display controlling unit 27 is able to three-dimensionally display, in a real-time manner, three-dimensional blood vessel images in which the tip of the advanced guide wire is located in the position at which the disparity is zero at all times.

Additional Function 2 of First Embodiment

In the first embodiment, the disparity image group generating unit 26 generates the group of disparity images at certain times, according to changes in the viewing direction. For example, when the C-arm has rotated, the disparity image group generating unit 26 obtains a new viewing direction from, for example, the C-arm controlling unit 25, so as to estimate a corresponding point and to generate a group of disparity images at certain times, based on the newly-obtained viewing direction. Further, the disparity image group generating unit 26 sends the newly-generated group of disparity images to the display controlling unit 27 at certain times. As a result, when the viewing direction changes due to the rotation of the C-arm, for example, the display controlling unit 27 is able to three-dimensionally display three-dimensional blood vessel images corresponding to the new viewing direction, as a stereoscopic roadmap image.

Additional Function 3 of First Embodiment

In the first embodiment, if the acquisition of the fluoroscopic image data is stopped while the stereoscopic roadmap image is being displayed, the display controlling unit 27 keeps the last frame in the fluoroscopic image data being displayed in the stereoscopic roadmap image (Last Image Hold (LIH)).

Advantageous Effects of First Embodiment

As explained above, according to the first embodiment, it is possible to three-dimensionally display the three-dimensional blood vessel images in the stereoscopic roadmap so as to provide a stereoscopic view, by using the two or more two-dimensional projection images generated from the three-dimensional blood vessel image data and by using the 3D monitor. Further, according to the first embodiment, the display positions in terms of the depth direction of the three-dimensional blood vessel images that are displayed three-dimensionally are determined based on the fluoroscopic image that is displayed two-dimensionally. More specifically, in the first embodiment, when the fluoroscopic image and the three-dimensional blood vessel images are displayed on the 3D monitor as being superimposed together, the group of disparity images is generated in such a manner that the disparity is zero at the point in the three-dimensional blood vessel image data corresponding to the point of interest in the fluoroscopic image. As a result, according to the first embodiment, it is possible to properly display the fluoroscopic image displayed two-dimensionally and the three-dimensional blood vessel images displayed three-dimensionally, while these images are superimposed together. Consequently, it is possible to display the medical image displayed two-dimensionally and the medical images displayed three-dimensionally in an easy-to-see manner.

For example, because the medical doctor is able to stereoscopically view the blood vessel positioned near the tip of the guide wire, it is possible to enhance the visibility of the important part. It is made easy for the medical doctor to understand the direction in which the guide wire should be advanced at a branching portion of a blood vessel, for example.

In other words, in addition to the advantageous effect where "it is easy to determine the direction in which the guide wire should be advanced" realized by the three-dimensional display, the spatial resolution of the reference point, which has no disparity, also becomes higher. As a result, the visibility of the important part where it is determined "in which direction the guide wire should be advanced hereafter" also becomes even higher.

Next, a second embodiment will be explained. A major difference from the first embodiment lies in the disparity image group generating process performed by the disparity image group generating unit 26. More specifically, in the first embodiment, the point of interest is extracted from the fluoroscopic image at the "first stage", whereas the corresponding point in the third-dimensional blood vessel image data that corresponds to the point of interest is estimated at the "second stage". In contrast, in the second embodiment, a corresponding point is directly specified, instead of estimating the corresponding point based on the point of interest in the fluoroscopic image. The "third stage" is the same as that in the first embodiment. In addition, the additional functions and the like that are explained in the first embodiment are similarly applicable to the second embodiment.

Next, methods for directly specifying the corresponding point in the second embodiment will be explained. Examples of the methods include "Method C1 by which fluoroscopic images taken from two directions are used", "Method C2 by which magnetism provided at the tip of the guide wire or the like is used", and "Method C3 by which a point of interest is designated by the operator on the display screen of the monitor 16". It is possible to use any of these methods in combination.

First, Method C1 will be explained. In the first embodiment, the method by which the coordinates of the guide wire tip are extracted from the fluoroscopic image was explained as Method A1. According to Method C1, the disparity image group generating unit 26 extracts the coordinates of the guide wire tip in the same manner as in Method A1, from the fluoroscopic images taken from the two directions. In this situation, because one set of coordinates of the guide wire tip is extracted from each of the fluoroscopic images taken from the mutually-different two directions, the disparity image group generating unit 26 calculates coordinates in a three-dimensional space from the two sets of coordinates of the guide wire tip by using an Epipolar theory. As a result, the disparity image group generating unit 26 obtains the calculated coordinates in the three-dimensional space as coordinates (x,y,z) of the corresponding point. In this situation, the disparity image group generating unit 26 may perform a coordinate conversion, as necessary, to convert the obtained coordinates (x,y,z) of the corresponding point into a coordinate system of the three-dimensional blood vessel image data.

Next, Method C2 will be explained. For example, an ablation treatment often uses a system called "electro-mapping system". In the "electro-mapping system", coordinates in a three-dimensional space is obtained in a magnetic field generated over a bed, by using magnetism provided at the tip of a guide wire or the like. In this situation, the disparity image group generating unit 26 is able to use the coordinates in the three-dimensional space obtained in the "electro-mapping system" as coordinates (x,y,z) of the corresponding point. In this situation, the disparity image group generating unit 26 may perform a coordinate conversion, as necessary, to convert the obtained coordinates (x,y,z) of the corresponding point into a coordinate system of the three-dimensional blood vessel image data. Further, it is possible to use a method of magnetic field generation equipment. In this situation, the magnetic field generation equipment is installed at the outside of the subject and generates a magnetic field. Coordinates in a three-dimensional space is obtained in a magnetic field generated, by using sensor provided at the tip of a guide wire or the like.

Next, Method C3 will be explained. For example, let us discuss a situation where, before a position alignment in the depth direction is performed, the operator has designated a point of interest on the display screen of the monitor 16, while the three-dimensional blood vessel images are displayed three-dimensionally on the monitor 16. In this situation, the disparity image group generating unit 26 identifies the point designated in the group of disparity images by the operator via the operating unit 21 from the three-dimensional blood vessel image data and obtains the identified coordinates as coordinates (x,y,z) of the corresponding point.

Next, a third embodiment will be explained. In the first and the second embodiments, the three-dimensional blood vessel images of the entirety of the three-dimensional blood vessel image data are displayed as the stereoscopic roadmap image. However, the disclosed embodiments are not limited to this example. For example, it is acceptable to display three-dimensional blood vessel images of only a part of the three-dimensional blood vessel image data. For example, it is acceptable to display three-dimensional blood vessel images of only an area positioned near a point of interest, out of the three-dimensional blood vessel image data.

Figure 11:
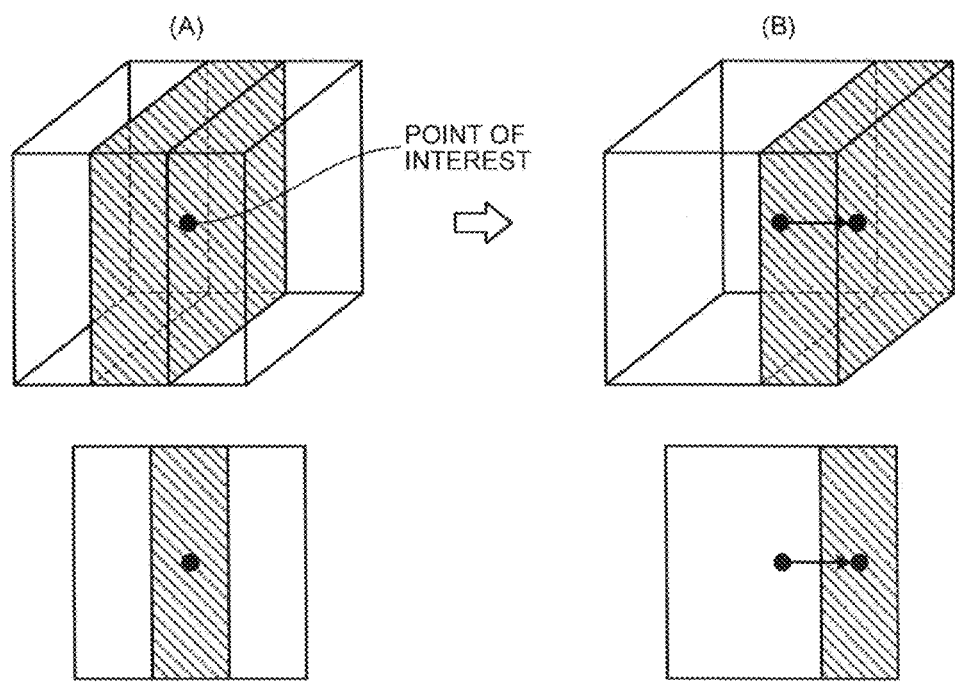
FIG. 11 is a drawing for explaining generation of a group of disparity images according to a third embodiment.

FIGS. 11 to 13 are drawings for explaining generation of a group of disparity images according to the third embodiment. In FIGS. 11 and 12, the two figures at the bottom respectively corresponding to the two figures at the top are each a side view of the three-dimensional blood vessel image data shown at the top. In the examples shown in FIGS. 11 and 12, the point of interest moves in a direction from the back of the display surface toward the front (see the black arrows in FIGS. 11 and 12).

In this situation, for example, the disparity image group generating unit 26 may generate a group of disparity images by using only such three-dimensional blood vessel image data that corresponds to a region of a certain width extending to the front and to the back of the point of interest, as shown in FIG. 11. When the point of interest has moved in the direction from the back of the display surface toward the front, the region having the certain width also moves following the point of interest, as shown in FIG. 11(B). Alternatively, another arrangement is also acceptable in which the display controlling unit 27 controls the display so as to render only such images that correspond to the region of a certain width extending to the front and to the back of the point of interest, from among the group of disparity images sent from the disparity image group generating unit 26. The region does not necessarily have to be in a rectangular shape as shown in FIG. 11 and may be, for example, in a circular shape formed around the point of interest.

In another example, as shown in FIG. 12, the disparity image group generating unit 26 may generate a group of disparity images by using only such three-dimensional blood vessel image data that corresponds to a region positioned in the advancing direction of the point of interest, while using the point of interest as a reference. When the point of interest has moved in a direction from the back of the display surface toward the front, the region used for generating the group of disparity images gradually becomes smaller, as shown in FIG. 12(B). Alternatively, another arrangement is also acceptable in which the display controlling unit 27 controls the display so as to render only such images that correspond to the region positioned in the advancing direction of the point of interest (so as not to display the unnecessary region in the direction opposite to the advancing direction), from among the group of disparity images sent from the disparity image group generating unit 26. The region does not necessarily have to be in a rectangular shape as shown in FIG. 12 and may be, for example, in a circular shape formed around the point of interest.

In yet another example, as shown in FIG. 13, the disparity image group generating unit 26 may generate a group of disparity images by using only such three-dimensional blood vessel image data that corresponds to a region near a treatment plan line. The treatment plan line is, as explained above, drawn by a medical doctor in advance, for example, to indicate that "the blood vessel in this area is to be treated". Also, the treatment plan line is rendered substantially along a blood vessel. Thus, as shown in FIG. 13 for example, the disparity image group generating unit 26 may generate a group of disparity images by using only a circular cylindrical region formed as being centered on the treatment plan line (e.g., a circular cylindrical region that has a diameter of 2 to 3 centimeters and uses the treatment plan line as the central axis thereof), from among the three-dimensional blood vessel image data.

As explained above, by displaying only the three-dimensional blood vessel images of the region positioned near the point of interest or the region positioned near the treatment plan line, the images other than those in the important part will not be seen by the viewer. As a result, it is possible to further enhance the visibility of the important part.

Next, a fourth embodiment will be explained. The exemplary embodiments above are explained while the "X-ray image" is used as an example of the medical image displayed two-dimensionally, whereas the "three-dimensional blood vessel image data" acquired in advance by an X-ray diagnosis apparatus or an X-ray CT apparatus is used as an example of the three-dimensional medical image data displayed three-dimensionally. However, the disclosed embodiments are not limited to these examples. In the fourth embodiment described below, an "ultrasound image" is assumed to be the medical image displayed two-dimensionally, whereas "three-dimensional medical image data" acquired in advance by an X-ray CT apparatus or a Magnetic Resonance Imaging (MRI) apparatus is assumed to be the three-dimensional medical image data displayed three-dimensionally. The various types of processes and the additional functions explained in the exemplary embodiments above are similarly applicable to the fourth embodiment.

Figure 14:
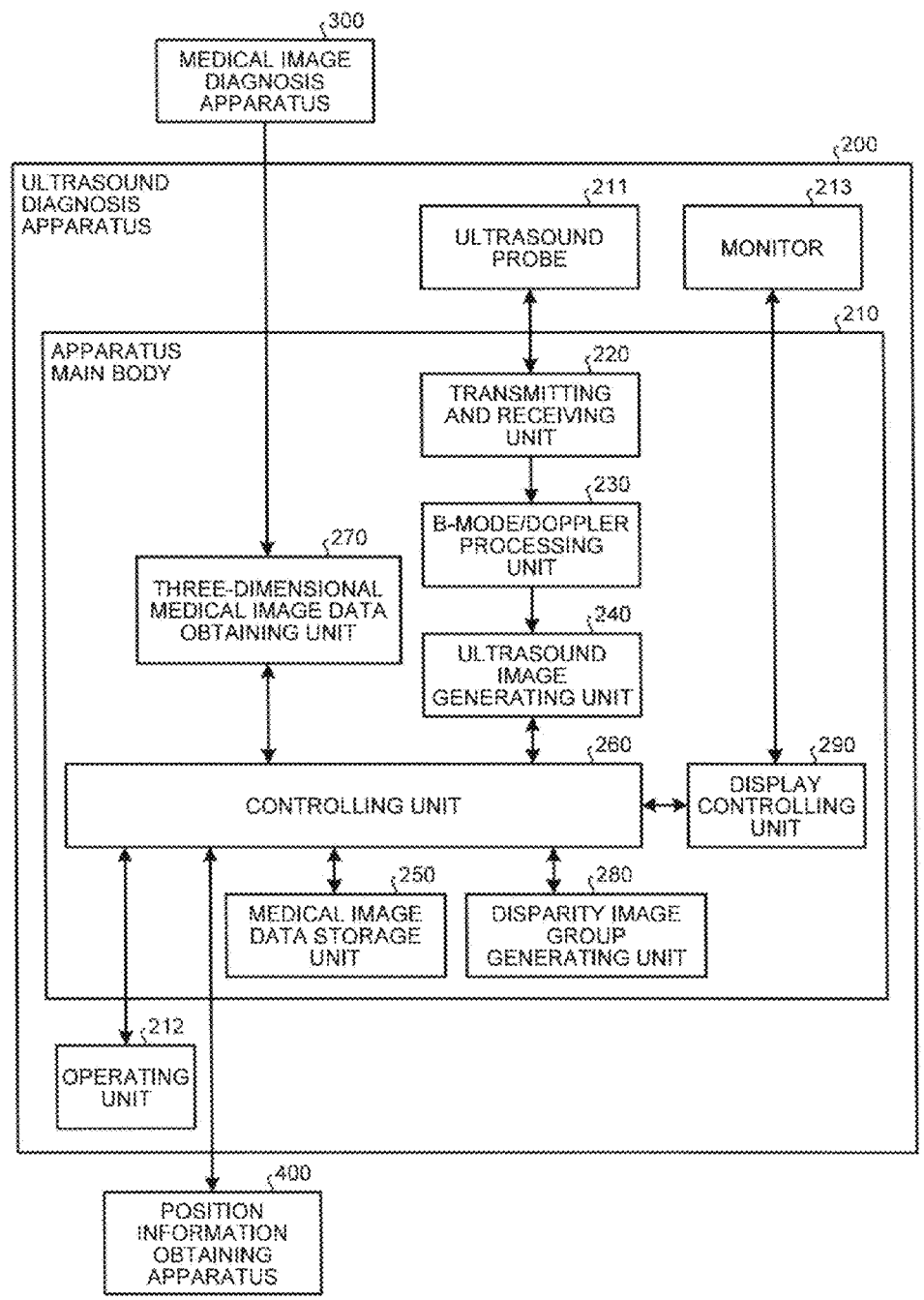
FIG. 14 is a drawing for explaining an exemplary configuration of an ultrasound diagnosis apparatus according to a fourth embodiment.

FIG. 14 is a drawing for explaining an exemplary configuration of an ultrasound diagnosis apparatus 200 according to the fourth embodiment. In the fourth embodiment, the ultrasound diagnosis apparatus 200 serving as a medical image display apparatus obtains three-dimensional medical image data from another medical image diagnosis apparatus 300 (e.g., an X-ray CT apparatus or an MRI apparatus) and displays a group of disparity images generated from the obtained three-dimensional medical image data and a two-dimensional ultrasound image acquired in a real-time manner, while these images are arranged side by side on a monitor 213. More specifically, as shown in FIG. 14, the ultrasound diagnosis apparatus 200 includes an apparatus main body 210, an ultrasound probe 211, an operating unit 212, and the monitor 213.

The ultrasound probe 211 includes a plurality of piezoelectric vibrators. The piezoelectric vibrators generate an ultrasound wave based on a drive signal supplied from a transmitting and receiving unit 220 (explained later). Further, the piezoelectric vibrators receive a reflected wave from the subject and convert the received reflected wave into an electric signal. The operating unit 212 is configured with a trackball, a switch, a button, and/or a touch command screen and is configured to receive inputs of various types of operations performed on the ultrasound diagnosis apparatus 200 from an operator. Like the monitor 16 described in the exemplary embodiments above, the monitor 213 is a 3D monitor with which the viewer is able to have a stereoscopic view of the images. For example, the monitor 213 displays the images three-dimensionally by using a shutter method.

In this situation, the ultrasound probe 211 according to the fourth embodiment includes a magnetic sensor. The magnetic sensor is connected to a position information obtaining apparatus 400 via an interface (not shown). Further, the magnetic sensor detects a three-dimensional magnetic field formed by using a transmitter (not shown) of the position information obtaining apparatus 400 as the origin, converts information of the detected magnetic field into a signal, and outputs the signal resulting from the conversion to the position information obtaining apparatus 400. Based on the signal received from the magnetic sensor, the position information obtaining apparatus 400 calculates the coordinates and the orientation of the magnetic sensor within a three-dimensional space formed by using the transmitter as the origin and sends the calculated coordinates and orientation to a controlling unit 260.

The apparatus main body 210 includes the transmitting and receiving unit 220, a B-mode/Doppler processing unit 230, an ultrasound image generating unit 240, a medical image data storage unit 250, the controlling unit 260, a three-dimensional medical image data obtaining unit 270, a disparity image group generating unit 280, and a display controlling unit 290.

The transmitting and receiving unit 220 includes a trigger generating circuit, a delaying circuit, and a pulser circuit and is configured to supply the drive signal to the ultrasound probe 211. The transmitting and receiving unit 220 also includes an amplifier circuit, an Analog/Digital (A/D) converter, and an adder and is configured to generate reflected-wave data by performing various types of processes on the reflected-wave signal received by the ultrasound probe 211.

The B-mode/Doppler processing unit 230 generates data (B-mode data) in which the strength of each signal is expressed by a degree of brightness, by performing a logarithmic amplification, an envelope detection process, and the like on the reflected-wave data received from the transmitting and receiving unit 220. Further, the B-mode/Doppler processing unit 230 extracts bloodstreams, tissues, and contrast echo components under the influence of the Doppler effect by performing a frequency analysis so as to obtain velocity information from the received reflected-wave data, and further generates data (Doppler data) obtained by extracting moving member information such as an average velocity, the dispersion, the power, and the like for a plurality of points.

The ultrasound image generating unit 240 generates the ultrasound image from the B-mode data or the Doppler data generated by the B-mode/Doppler processing unit 230. More specifically, the ultrasound image generating unit 240 generates the display-purpose ultrasound image (the B-mode image or the Doppler image) from the B-mode data or the Doppler data, by converting (by performing a scan convert process) a scanning line signal sequence from an ultrasound scan into a scanning line signal sequence in a video format used by, for example, television.

The medical image data storage unit 250 stores therein, for example, the three-dimensional medical image data obtained by the three-dimensional medical image data obtaining unit 270 from the other medical image diagnosis apparatus 300. The controlling unit 260 exercises overall control of the ultrasound diagnosis apparatus 200.

The three-dimensional medical image data obtaining unit 270 obtains the three-dimensional medical image data from the other medical image diagnosis apparatus 300 directly, or via a network, or via an input of the operator or the like.

The disparity image group generating unit 280 generates right-eye images and left-eye images serving as a group of disparity images, from the three-dimensional blood vessel image data. The disparity image group generating process performed by the disparity image group generating unit 280 is the same as the disparity image group generating process performed by the disparity image group generating unit 26 according to the first embodiment. In other words, the disparity image group generating unit 280 extracts a point of interest (e.g., a tip end of a puncture needle rendered in the ultrasound image) from the ultrasound image, estimates a corresponding point in the three-dimensional medical image data that corresponds to the point of interest, and generates the group of disparity images in such a manner that the estimated corresponding point coincides with the reference point.

In this situation, the estimation of the corresponding point in the three-dimensional medical image data that corresponds to the point of interest extracted from the ultrasound image is performed based on the premise that the coordinate systems are brought into correspondence with each other between the three-dimensional medical image data acquired by the other medical image diagnosis apparatus 300 and the ultrasound image. The process of bringing the coordinate systems into correspondence with each other is equivalent to an axis alignment process performed between the three axes of the three-dimensional medical image data and the three axes of the magnetic field coordinate system of the ultrasound probe 211. More specifically, for example, first, while the ultrasound probe 211 to which the magnetic sensor is attached is placed on the subject perpendicularly, a set button is pressed. Thus, the orientation of the magnetic sensor at that time is set as the vertical direction. After that, an ultrasound image rendering the same feature portion as a feature portion rendered in the three-dimensional medical image data is selected, and the set button is pressed again. Thus, the coordinates of the magnetic sensor at that time and the coordinates of the three-dimensional medical image data are brought into correspondence with each other. The feature portion may be, for example, a blood vessel or the xiphoid process. As a result, the coordinates of the three-dimensional medical image data and the coordinates of the ultrasound image are brought into correspondence with each other, so that it is possible to estimate the coordinates of the corresponding point in the three-dimensional medical image data, based on the coordinates of the point of interest extracted from the ultrasound image.

The display controlling unit 290 displays the group of disparity images and the ultrasound image that are arranged side by side on the monitor 213. The display controlling unit 290 is able to display the ultrasound image two-dimensionally by, for example, arranging the right-eye image to be the same as the left-eye image. For example, the display controlling unit 290 three-dimensionally displays a CT image represented by the group of disparity images on the left half of the monitor 213 and two-dimensionally displays the ultrasound image acquired in a real-time manner on the right half of the monitor 213. In other words, at a time to display a right-eye image, the display controlling unit 290 displays the ultrasound image generated by the ultrasound image generating unit 240 and the right-eye image sent from the disparity image group generating unit 280 that are arranged side by side on the monitor 213. In contrast, at a time to display a left-eye image, the display controlling unit 290 displays the ultrasound image generated by the ultrasound image generating unit 240 and the left-eye image sent from the disparity image group generating unit 280 that are arranged side by side on the monitor 213.

In the fourth embodiment, the example is explained in which the group of disparity images and the ultrasound image are displayed while being arranged side by side on the monitor 213. However, the disclosed embodiments are not limited to this example. As explained in the first to the third embodiments, it is also acceptable to display the group of disparity images and the ultrasound image that are superimposed together.

The first to the fourth embodiments described above are only examples, and it is possible to implement the exemplary embodiments in other various modes.

In the first to the third embodiments, the examples are explained in which the fluoroscopic image and the three-dimensional blood vessel images are displayed while being superimposed together. In that situation, for example, it is acceptable to display the fluoroscopic image in a gray scale and to display the three-dimensional blood vessel images in color. In other words, it is acceptable to display in a gray scale the X-ray image that is displayed two-dimensionally and to display in color the group of disparity images that is displayed three-dimensionally so as to display these images while being superimposed together. The same applies to the fourth embodiment. For example, it is acceptable to display the ultrasound image in a gray scale and to display the three-dimensional blood vessel images in color.

Further, the exemplary embodiments above are explained while using the position of the tip of the guide wire or a catheter or the position of a stent, a balloon, or a valve as an example of the "point of interest"; however, the disclosed embodiments are not limited to these examples. The "point of interest" may be an end of, for example, a gastrocamera, an intracavity probe, (e.g., a transesophageal probe, a transrectal probe), a puncture needle, or the like. The "point of interest" may be referred to as a "feature point".

Further, in the exemplary embodiments above, the examples are explained in which the "X-ray image" and the "three-dimensional blood vessel image data acquired by the X-ray diagnosis apparatus or the X-ray CT apparatus" are displayed while being superimposed together and in which the "ultrasound image" and the "three-dimensional medical image data acquired by the X-ray CT apparatus or the MRI apparatus" are displayed while being arranged side by side; however, the disclosed embodiments are not limited to these examples. In other words, the disclosed embodiments are not limited by the image-taking target or the medical image diagnosis apparatus used for acquiring the medical image data. The exemplary embodiments are similarly applicable to any other situation where a medical image obtained by taking an image of a target object is two-dimensionally displayed, while three-dimensional medical image data obtained by taking images of the same target object is three-dimensionally displayed (including the situation where the images are displayed while being superimposed together or while being arranged side by side).

Further, the exemplary embodiments above are explained by using the "fluoroscopic image" displayed two-dimensionally in a real-time manner or the "ultrasound image" displayed two-dimensionally in a real-time manner; however, the disclosed embodiments are not limited to these examples. The medical image displayed two-dimensionally does not necessarily have to be a moving image displayed in a real-time manner and may be a medical image acquired in the past or may be a still image.

Further, in the exemplary embodiments described above, the examples are explained in which the medical image display apparatus represented by the medical image diagnosis apparatus such as the X-ray diagnosis apparatus, the ultrasound diagnosis apparatus, or the like determines the display position of the group of disparity images, generates the group of disparity images, and displays the medical image and the group of disparity images that are superimposed together or that are arranged side by side; however, the disclosed embodiments are not limited to these examples. For example, the processes described above may be performed by a medical image display apparatus such as a workstation, a viewing tool used in a Picture Archiving and Communication System (PACS), or any of various types of devices used in an electronic medical record system. In that situation, the medical image display apparatus may obtain the medical image displayed two-dimensionally and the three-dimensional medical image data displayed three-dimensionally or the like, directly from a medical image diagnosis apparatus, or via a network, or via an input of the operator, or the like.

The constituent elements of the apparatuses shown in the drawings are based on functional concepts. Thus, it is not necessary to physically configure the elements as indicated in the drawings. In other words, the specific mode of distribution and integration of the apparatuses is not limited to those shown in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a Central Processing Unit (CPU) and a computer program that is analyzed and executed by the CPU or may be realized as hardware using wired logic.

It is possible to realize the display controlling method explained in any of the exemplary embodiments above by causing a computer such as a personal computer or a workstation to execute a display controlling computer program prepared in advance. It is possible to distribute such an image processing computer program via a network such as the Internet. Further, the computer program may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, and may be executed as being read by a computer from the recoding medium.

When the X-ray diagnosis apparatus according to at least one of the exemplary embodiments described above is used, it is possible to properly display the medical image displayed two-dimensionally and the medical images displayed three-dimensionally while these images are superimposed together.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image display apparatus comprising:
   a display unit configured to three-dimensionally display a right-eye image and a left-eye image generated from three-dimensional medical image data acquired from a subject so as to provide a stereoscopic view, and to two-dimensionally display a medical image that is a different image acquired from the subject so as to provide a planar view;
   a generating unit configured to determine a position of a reference point at which a disparity among the right-eye image and the left-eye image is zero in terms of a depth direction with respect to a display surface of the display unit, based on the medical image, and to generate the right-eye image and the left-eye image from the three-dimensional medical image data so as to realize the determined position; and
   a display controlling unit configured to perform registration of the three-dimensional medical image data and the medical image, and to display, on the display unit, a first superimposed image formed by superimposing the right-eye image generated from the three-dimensional image data and the medical image, and a second superimposed image formed by superimposing the left-eye image generated from the three-dimensional image data and the medical image, alternately.

2. An X-ray diagnosis apparatus comprising:
   a display unit configured to three-dimensionally display a group of disparity images generated from three-dimensional medical image data acquired from a subject so as to provide a stereoscopic view, and to two-dimensionally display an X-ray image that is a different image acquired from the subject so as to provide a planar view;
   an acquiring unit configured to acquire the X-ray image; and
   a display controlling unit configured to perform registration of the three-dimensional medical image data and the X-ray image, and to display, on the display unit, superimposed image formed by superimposing the X-ray image and the group of disparity images generated from the three-dimensional medical image data.

3. A medical apparatus comprising:
   a display unit configured to three-dimensionally display a group of disparity images generated from three-dimensional medical image data acquired from a subject so as to provide a stereoscopic view, and to two-dimensionally display a medical image that is a different image acquired from the subject so as to provide a planar view; and a display controlling unit configured to perform registration of the three-dimensional medical image data and the medical image, and to display, on the display unit, superimposed image formed by superimposing the group of disparity images generated from the three-dimensional medical image data and the medical image.

4. The medical apparatus according to claim 3, wherein the display controlling unit displays, on the display unit, a first superimposed image formed by superimposing the right-eye image generated from the three-dimensional image data and the medical image, and a second superimposed image formed by superimposing the left-eye image generated from the three-dimensional image data and the medical image, alternately.

5. The medical apparatus according to claim 3, wherein the medical apparatus further comprises:

a generating unit configured to determine a display position of the group of disparity images to be three-dimensionally displayed on the display unit in terms of a depth direction with respect to a display surface of the display unit and to generate the group of disparity images from the three-dimensional medical image data so as to realize the determined display position;

the generating unit determines the display position of the group of disparity images, based on the medical image displayed two-dimensionally on the display unit.

6. The medical apparatus according to claim 5, wherein the generating unit generates the group of disparity images from the three-dimensional medical image data in such a manner that a corresponding point in the three-dimensional medical image data that corresponds to a feature point in the medical image is positioned near a reference point at which a disparity among the group of disparity images is zero.

7. The medical apparatus according to claim 6, wherein the generating unit generates the group of disparity images from the three-dimensional medical image data in such a manner that the corresponding point in the three-dimensional medical image data that corresponds to the feature point in the medical image coincides with a reference point at which the disparity among the group of disparity images is zero.

8. The medical apparatus according to claim 6, wherein the generating unit generates the group of disparity images by calculating the corresponding point in the three-dimensional medical image data that corresponds to the feature point in the medical image and performing a rendering process on the three-dimensional medical image data according to the calculated corresponding point.

9. The medical apparatus according to claim 6, wherein the generating unit obtains the feature point in the medical image by extracting an image of a tool from the medical image through image processing applied to the medical image and extracting a tip of the tool based on a shape of the extracted image.

10. The medical apparatus according to claim 6, wherein the generating unit obtains the feature point in the medical image by receiving a designation from an operator of the medical image display apparatus, on a display screen of the display unit.

11. The medical apparatus according to claim 6, wherein the three-dimensional medical image data and the medical image are acquired by an X-ray diagnosis apparatus, and the generating unit calculates the corresponding point in the three-dimensional medical image data that corresponds to the feature point, by searching through the three-dimensional medical image data along a straight line that connects coordinates of the feature point in the medical image to coordinates of an X-ray source and identifying an intersection point at which the straight line intersects a luminal region in the three-dimensional medical image data.

12. The medical apparatus according to claim 6, wherein the three-dimensional medical image data and the medical image are acquired by an X-ray diagnosis apparatus, and the generating unit extracts an image of a tool from each of medical images taken from mutually-different two directions through image processing applied to each of the medical images, obtains a feature point in each of the medical images by calculating coordinates of a tip of the tool from each of the medical images based on shapes of the extracted images, and calculates corresponding points in the three-dimensional medical image data that respectively correspond to the feature points by using the coordinates of the tip calculated from each of the medical images.

13. The medical apparatus according to claim 6, wherein the generating unit obtains coordinates of a tip of a tool within a three-dimensional space with respect to the tool rendered in the medical image by using magnetism and calculates the corresponding point in the three-dimensional medical image data that corresponds to the feature point based on the obtained coordinates within the three-dimensional space.

14. The medical apparatus according to claim 6, wherein the generating unit calculates the corresponding point in the three-dimensional medical image data that corresponds to the feature point by receiving a designation from an operator of the medical image display apparatus, on a display screen of the display unit.

15. The medical apparatus according to claim 6, wherein the generating unit follows the feature point in the medical image and generates the group of disparity images at certain times according to a movement of the feature point.

16. The medical apparatus according to claim 7, wherein the generating unit generates the group of disparity images by calculating the corresponding point in the three-dimensional medical image data that corresponds to the feature point in the medical image and performing a rendering process on the three-dimensional medical image data according to the calculated corresponding point.

17. The medical apparatus according to claim 7, wherein the generating unit obtains the feature point in the medical image by extracting an image of a tool from the medical image through image processing applied to the medical image and extracting a tip of the tool based on a shape of the extracted image.

18. The medical apparatus according to claim 7, wherein the three-dimensional medical image data and the medical image are acquired by an X-ray diagnosis apparatus, and the generating unit calculates the corresponding point in the three-dimensional medical image data that corresponds to the feature point, by searching through the three-dimensional medical image data along a straight line that connects coordinates of the feature point in the medical image to coordinates of an X-ray source and identifying an intersection point at which the straight line intersects a luminal region in the three-dimensional medical image data.

19. The medical apparatus according to claim 7, wherein
the three-dimensional medical image data and the medical image are acquired by an X-ray diagnosis apparatus, and
the generating unit extracts an image of a tool from each of medical images taken from mutually-different two directions through image processing applied to each of the medical images, obtains a feature point in each of the medical images by calculating coordinates of a tip of the tool from each of the medical images based on shapes of the extracted images, and calculates corresponding points in the three-dimensional medical image data that respectively correspond to the feature points by using the coordinates of the tip calculated from each of the medical images.

20. The medical apparatus according to claim 7, wherein
the generating unit obtains coordinates of a tip of a tool within a three-dimensional space with respect to the tool rendered in the medical image by using magnetism and calculates the corresponding point in the three-dimensional medical image data that corresponds to the feature point based on the obtained coordinates within the three-dimensional space.

21. The medical apparatus according to claim 7, wherein
the generating unit follows the feature point in the medical image and generates the group of disparity images at certain times according to a movement of the feature point.

* * * * *